United States Patent [19]

Vogt

[11] Patent Number: 4,518,539

[45] Date of Patent: May 21, 1985

[54] PROCESS FOR MAKING ACETIC ANHYDRIDE

[76] Inventor: Wilhelm Vogt, Bellerstrasse 74, Hürth, Fed. Rep. of Germany

[21] Appl. No.: 515,355

[22] Filed: Jul. 19, 1983

[30] Foreign Application Priority Data

Aug. 14, 1982 [DE] Fed. Rep. of Germany ....... 3230307

[51] Int. Cl.$^3$ ............................................. C07C 51/56
[52] U.S. Cl. ................................................... 260/549
[58] Field of Search ........................................ 260/549

[56] References Cited

U.S. PATENT DOCUMENTS 2,730,546  1/1956  Reppe et al. ......................... 562/519
4,430,506  2/1984  Gauthier-Lafaye et al. ........ 562/519

Primary Examiner—Natalie Trousof
Assistant Examiner—L. Hendriksen

[57] ABSTRACT

The disclosure relates to a process for making acetic anhydride wherein methyl acetate and/or dimethylether (is) are reacted with carbon monoxide under practically anhydrous conditions at temperatures of 390° to 540° K., under pressures of 1 to 300 bars in the presence of a catalyst system comprised of noble metals belonging to group VIII of the Periodic System of the elements or their compounds, iodine and/or its compounds and a tertiary or quaternary organic nitrogen, phosphorus, arsenic or antimony compound. More particularly, use is made of a catalyst system containing vanadium or niobium or their compounds as additional constituents, the catalyst system being used in combination with reaction gas containing carbon monoxide and 5 to 30 volume % hydrogen.

3 Claims, No Drawings

PROCESS FOR MAKING ACETIC ANHYDRIDE

A process for making acetic anhydride from acetic acid methyl ester (methyl acetate) and carbon monoxide, wherein the reactants are passed under pressures of 1 to 500 bars and at temperatures of 50° to 250° C. (323°-523° K.) over catalysts containing noble metals belonging to group VIII of the Periodic System or their compounds, as well as iodine and/or iodine compounds has already been described in German Patent Specificaton DE-OS No. 24 50 965 A 1. Promotors used in this reaction are selected from alkyl or aryl phosphine or organic nitrogen compounds, such as pyridines, pyrrolidones, alkyl amines or N-alkyl derivatives of aniline. Further potential promotors include carbonyl-yielding metals or their compounds, e.g. cobalt, nickel or iron. The presence of relatively large proportions, e.g. 5 to 50 volume %, of hydrogen has often been found favorably to influence the course of the reaction. Dimethylether yielding methyl acetate under the reaction conditions can also be used.

A further process for making acetic anhydride has been described in European Patent EP-PS 8 396 B 1, wherein at least one heterocyclic aromatic compound in which at least one hetero atom is a quaternary nitrogen atom and of which the melting or mixed melting point is lower than 413 K, this being the boiling point of acetic anhydride, is used as a promotor and the reaction is additionally effected in the presence of an aliphatic carboxylic acid having from 1 to 8 carbon atoms. Here again, it is possible to use carbon monoxide/hydrogen-mixtures containing up to 10 volume % hydrogen. The useful feed materials are selected from methyl acetate and/or dimethylether.

A still further process for making acetic anhydride from methyl acetate or dimethylether, CO, an iodide or bromide under practically anhydrous conditions and in the presence of a catalyst containing noble metals belonging to group VIII of the Periodic System, and in the presence of a multiple promoter containing a metal belonging to group IVA, VA or VIA of the Periodic System as well as an organonitrogen compound or organophosphorus compound with trivalent nitrogen and phosphorus therein, has inter alia been described in German Patent DE-PS No. 26 10 036 C 2. The process is effected in the presence of at most traces of hydrogen (cf. column 5, lines 46-51). As disclosed in Examples 20 and 21 of that Patent, rhodium trichloride is used together with triphenyl phosphine and vanadium acetylacetonate or together with metallic niobium as a promoter. All other of the altogether 24 examples use rhodium trichloride alone as the noble metal catalyst.

As results from the statements made hereinabove, it is known art (cf. DE-OS No. 24 50 965 A 1) to effect the reaction, if desired in the presence of relatively large proportions of hydrogen, however in the absence of vanadium or niobium, and it is also known art (cf. DE-PS No. 26 10 036 C2) to effect the reaction in the absence of hydrogen, however in the presence of vanadium or niobium.

We have now unexpectedly found that by combining the two methods just referred to, i.e. by effecting the reaction in the presence of considerable proportions of water and with the use of vanadium or niobium, it is possible significantly to increase the catalyst efficiency, especially in those cases in which palladium or one of its compounds is used as the noble metal. This is an highly unexpected result in view of comparative Examples 1 and 2 hereinafter according to which the catalyst efficiency was only moderately increased absolutely from about 20 to about 54 g acetic anhydride per gram palladium per hour in all those cases in which a vanadium promotor was added to a palladium catalyst (Pd:V = 1:1.5) in the absence of hydrogen under otherwise identical reaction conditions. The working method disclosed in comparative Example 2 falls under the claims of DE-PS No. 10 036 C2. Comparative Example 3 was inversely carried out under the reaction conditions described in DE-OS No. 24 50 965 A, i.e. a palladium catalyst was used without vanadium promoter but in the presence of hydrogen, and about 113 g acetic anhydride per gr Pd per hour was obtained. In working Example 4 described this invention, the two methods described in comparative Examples 2 and 3 were combined with the unexpected effect that the catalyst efficiency increased to 833 g acetic anhydride per g Pd per hour. The selectivity for acetic anhydride formation was approximately 90%.

The present invention relates more particularly to a process for making acetic anhydride by reacting methyl acetate and/or dimethylether with carbon monoxide under practically anhydrous conditions at temperatures of 390 to 540 K, under pressures of 1 to 300 bars in the presence of a catalyst system comprised of noble metals belonging to group VIII of the Periodic System of the elements or their compounds, iodine and/or its compounds and a tertiary or quaternary organic nitrogen, phosphorus, arsenic or antimony compound which comprises: using a catalyst system containing vanadium or niobium or their compounds as additional constituents, this catalyst system being used in combination with reaction gas containing carbon monoxide and 5 to 30 volume % hydrogen. A preferred feature provides for the methyl acetate or dimethylether/noble metal(compound)/iodine(compound)/nitrogen, phosphorus, arsenic or antimony compound/vanadium(compound) or niobium(compound) to be used in a molar ratio of 1:(0.0001-0.01): (0.01-1):(0.01-1):(0.0001-0.1).

By means of the hydrogen, the reaction system is rendered highly active. The reaction gas should preferably contain 5 to 15 volume % $H_2$ and 95 to 85 volume % CO.

Palladium should most preferably be used as the noble metal belonging to group VIII of the Periodic System, but rhodium can also be used. It is preferable to use these two metals in the form of their chlorides or acetates, e.g. $PdCl_2$, $Pd(CH_3COO)$, $RhCl_3 \cdot xH_2O$.

Methyl iodide or hydrogen iodide should preferably be used as iodine compound. The tertiary organonitrogen or organo-phosphorus compounds comprise amines, phosphines or aminophosphines, preferably trialkylamines, N,N-dialkylaniline, pyridine, trialkyl or triarylphosphines, especially N-methylimidazol, 3-picoline, 2,4-lutidine, 3,4-lutidine, quinoline, tributylphosphine, trioctylphosphine, trilaurylphosphine or triphenylphosphine. Organonitrogen or organophosphorus compounds quaternized with methyl halides or hydrogen halide, e.g. N-methylpyridinium halide,N,N-dimethylimidazolium halide, N-methyl-3-picolinium halide, N-methyl-2,4-lutidinium halide, N-methyl-3,4-lutidinium halide, N-methylquinolinium halide, tributyl-methylphosphonium halide, trioctyl-methylphosphonium halide, trilauryl-methylphosphonium halide, triphenyl-methylphosphonium halide, the halide being in each case the chloride, bromide or preferably iodide, can also be used. The organic arsenic and antimony compounds preferably comprise arsines and stibines.

The useful vanadium and niobium compounds include, e. g. the chlorides ($VCl_3$, $NbCl_5$) or acetylacetonates ($V(C_5H_7O_2)_3$). The noble metal belonging to group VIII of the Periodic System and vanadium or niobium should preferably be used in a molar ratio of (1:0.5) to (1:20).

The process of this invention should preferably be carried out at temperatures of 400° to 475° K. under pressures of 20 to 150 bars.

It is also possible for the present carbonylation reaction to be carried out in the presence of a solvent which should conveniently be selected from acetic acid or amides, such as N-methylpyrrolidone, N,N-diethylacetamide or sulfur-containing solvents, such as sulfolane.

The effect produced by the Pd/V-system is of special commercial interest as the geological resources of palladium are approximately 15 times larger than those of rhodium. In other words the present process which is characterized by the combination of the steps described hereinabove permits the catalyst price to be considerably reduced.

Despite the presence of hydrogen, the selectivity for formation of methane, based on the CO used, is less than 1%, whereas the selectivity for acetic anhydride, based on the methyl acetate or dimethylether converterd, is approximately 90%.

EXAMPLE 1

Comparative Example 250 g methyl acetate, 1.06 g $PdCl_2$, 50 g methyl iodide and 102 g methyl-tributylphosphonium iodide were reacted with CO at 455° K. under a pressure of 100 bars in a Hastelloy autoclave. 44 g acetic anhydride, corresponding to 19.76 g $Ac_2O$ per gram Pd per hour, was obtained after a reaction period of 3.5 hours.

EXAMPLE 2

Comparative Example 250 g methyl acetate, 1.06 g $PdCl_2$, 1.39 g vanadium-(III)-chloride, 50 g $CH_3I$ and 102 g methyl-tributylphosphonium iodide were reacted with CO at 455° K. under a pressure of 100 bars in a Hastelloy autoclave. 75.3 g acetic anhydride, corresponding to 53.8 g $Ac_2O$ per gram Pd per hour, was obtained after 2.2 hours.

EXAMPLE 3

Comparative Example 250 g (3.38 mols) methyl acetate, 50 g (0.352 mol) $CH_3I$, 1.06 g (6 millimols) $PdCl_2$ and 102 g (0.296 mol) methyltributylphosphonium iodide were reacted with a $CO/H_2$-mixture (molar ratio=10:1) at 455° K. under a pressure of 100 bars in a Hastelloy autoclave. 108 g (1.06 mol) acetic anydride, corresponding to 113.2 g $Ac_2O$ per gram Pd per hour, was obtained after 1.5 hours. 106.2 g (1.44 mol) unreacted methyl acetate was recovered. The selectivity was 54.7%.

EXAMPLE 4

250 g (3.38 mols) methyl acetate, 1.06 g (6 millimols) $PdCl_2$, 1.39 g ( 9 millimols) $VCl_3$, 50 g (0.352 mol) methyl iodide and 102 g (0.296 mol) methyl-tributylphosphonium iodide were reacted with a $CO/H_2$-mixture (molar ratio=10:1) at 455° K. under 100 bars. 171.8 g (1.68 mol) acetic anhydride, corresponding to 853 g $Ac_2O$ per gram Pd per hour together with traces of ethylidene diacetate was obtained after a reaction period of 19 minutes. 111.5 g (1.51 mol) unreacted methyl acetate was recovered. The selectivity was 89.5%.

EXAMPLE 5

250 g methyl acetate, 1.06 g $PdCl_2$, 3.2 g (12 millimols) niobium(V)-chloride, 50 g methyl iodide and 102 g methyltributylphosphonium iodide were reacted with a $CO/H_2$-mixture (molar ratio=10:1) at 455° K. under 100 bars. 139 g acetic anhydride, corresponding to 291.4 g $Ac_2O$ per gram Pd per hour, was obtained after 45 minutes.

The rhodium(III)chloride used in the following Examples was hydrate ($RhCl_3 . x H_2O$) containing 38.2 wgt % Rh.

EXAMPLE 6

Comparative Example 250 g methyl acetate, 50 g methyl iodide, 68 g N,N-dimethylimidazolium iodide, 1.6 g $RhCl_3$ and 1.86 g vanadium (III)chloride were reacted with CO at 435° K. under 100 bars. 182 g acetic anhydride, corresponding to 596.7 g $Ac_2O$ per gram Rh per hour, was obtained after 30 minutes.

EXAMPLE 7

250 g (3.38 mols) methyl acetate, 50 g (0.352 mol) methyl iodide, 68 g (0.303 mol) N,N-dimethylimidazolium iodide, 1.6 g $RhCl_3$ (5.9 millimols Rh) and 1.86 g (11.8 millimols) $VCl_3$ were reacted with a $CO/H_2$-mixture (molar ratio=10:1) at 435° K. under 100 bars. 180 g (1.76 mol) acetic anhydride, corresponding to 769.8 g $Ac_2O$ per gram Rh per hour together with traces of ethylidene diacetate was obtained after 23 minutes. 98 g (1.32 mol) unreacted methylacetate was recovered. The selectivity was 85.5%.

We claim:

1. A process for making acetic anhydride which comprises reacting methyl acetate or dimethylether with a gas contaning carbon monoxide and 5 to 30 volume % hydrogen under practically anhydrous conditions at temperatures of 390° to 540° K., under pressures of 1 to 300 bars in the presence of a catalyst system consisting essentially of noble metals belonging to group VIII of the Periodic System of the elements or their compounds, vanadium or niobium or their compounds, iodine or its compounds and a tertiary or quaternary organic compound selected from the group consisting of compounds of nitrogen, phosphorus, arsenic or antimony.

2. A process as claimed in claim 1, wherein the methyl acetate or dimethylether/noble metal(compound)/iodine(compound)/nitrogen, phosphorus, arsenic or antimony compound/vanadium(compound) or niobium(compound) are used in a molar ratio of 1:(0.0001–0.01):(0.01–1): (0.01–1):(0.0001–0.1).

3. A process for making acetic anhydride from methyl acetate or dimethyl ether, comprising:
   reacting under essentially anhydrous conditions at temperatures of 390° to 540° K. and under pressures of 1 to 300 bars, methyl acetate or dimethylether with a reaction gas comprising carbon monoxide and 5 to 30 volume % hydrogen, in the presence of a catalyst system;
   said catalyst system consisting essentially of palladium or rhodium or their compounds, iodine or its compounds, a tertiary or quaternary organic compound selected from the group consisting of compounds of nitrogen, phosphorus, arsenic, or antimony, and vanadium or niobium or their compounds; and recovering acetic anhydride as the product of the reaction.

* * * * *